United States Patent
Breuch et al.

(10) Patent No.: US 9,233,196 B2
(45) Date of Patent: Jan. 12, 2016

(54) METHOD FOR PRE-FILLING A HEMODIALYSIS APPARATUS

(71) Applicant: D_MED CONSULTING AG, Krefeld (DE)

(72) Inventors: Gerd Breuch, Troisdorf (DE); Frank Biermann, Hamburg (DE); Yoji Yanagimoto, Moorsel (BE)

(73) Assignee: D_MED CONSULTING AG, Krefeld (DE)

( * ) Notice: Subject to any disclaimer, the term of this patent is extended or adjusted under 35 U.S.C. 154(b) by 75 days.

(21) Appl. No.: 13/889,372

(22) Filed: May 8, 2013

(65) Prior Publication Data

US 2013/0303963 A1    Nov. 14, 2013

(30) Foreign Application Priority Data

May 9, 2012   (EP) .................................... 12167382

(51) Int. Cl.
*A61M 1/14*    (2006.01)
*A61M 1/34*    (2006.01)
(Continued)

(52) U.S. Cl.
CPC ............... *A61M 1/30* (2013.01); *A61M 1/3465* (2014.02); *A61M 1/365* (2014.02); *A61M 1/3621* (2013.01);
(Continued)

(58) Field of Classification Search
CPC . A61M 1/3643; A61M 1/365; A61M 1/3649; A61M 1/30; A61M 2205/3331; A61M 1/3644; A61M 1/3621; A61M 1/3624; A61M 1/3627; A61M 1/3629; A61M 1/3632; A61M 1/3639; A61M 1/3647; A61M 1/16; A61M 1/1601; A61M 1/3465; A61M 2205/01; A61M 2205/3351; A61M 2205/3355; A61M 2205/15; A61M 2205/3334
See application file for complete search history.

(56) References Cited

U.S. PATENT DOCUMENTS 4,324,662 A    4/1982  Schnell
5,178,603 A    1/1993  Prince
(Continued)

FOREIGN PATENT DOCUMENTS

DE    34 42 744 A1    6/1986
DE    694 17 608       9/1999
(Continued)

OTHER PUBLICATIONS

Gambro: "Artis Operator's Manual", Code 6992739, Rev. C, pp. 3-31, 3-33, 4-32, 16-37, 16-67, 16-69, 16-71 (2009).
(Continued)

*Primary Examiner* — Adam Marcetich
(74) *Attorney, Agent, or Firm* — Norman B. Thot

(57) ABSTRACT

A method for pre-filling a hemodialysis apparatus includes providing a hemodialysis apparatus comprising a pre-filling liquid source which supplies a pre-filling liquid, a dialyzer, a dialysate side, a blood side. The dialysate side comprises a dialysate chamber, a dialysate pump to pump the pre-filling liquid to the dialysate chamber, and a waste pump to pump the pre-filling liquid away from the dialysate chamber. The blood side comprises an arterial line, a blood pump, a blood chamber of the dialyzer, and a venous line. A pressure sensor is arranged on the dialysate side or on the blood side. The arterial line and the venous line are pre-filled with the pre-filling liquid via the dialysate pump. A blood-side fluid pressure is continuously determined via the pressure sensor during the pre-filling. The pre-filling is stopped when the blood-side fluid pressure determined by the pressure sensor exceeds or falls below a defined limit pressure.

12 Claims, 2 Drawing Sheets

(51) Int. Cl.
*A61M 1/30* (2006.01)
*A61M 1/36* (2006.01)

(52) U.S. Cl.
CPC ........... *A61M 1/3627* (2013.01); *A61M 1/3643* (2013.01); *A61M 1/3644* (2014.02); *A61M 1/3647* (2014.02); *A61M 1/3649* (2014.02); *A61M 2205/3331* (2013.01); *A61M 2205/3334* (2013.01); *A61M 2205/3351* (2013.01); *A61M 2205/3355* (2013.01)

(56) References Cited

U.S. PATENT DOCUMENTS

| | | | |
|---|---|---|---|
| 5,259,961 | A | 11/1993 | Eigendorf |
| 5,591,344 | A | 1/1997 | Kenley et al. |
| 5,650,071 | A | 7/1997 | Brugger et al. |
| 5,679,245 | A | 10/1997 | Manica |
| 5,776,345 | A | 7/1998 | Truitt et al. |
| 5,863,421 | A | 1/1999 | Peter, Jr. et al. |
| 5,893,382 | A * | 4/1999 | Puppini ................. A61M 1/168 134/169 R |
| 6,083,187 | A | 7/2000 | Nakayama et al. |
| 6,187,198 | B1 * | 2/2001 | Utterberg ....................... 210/645 |
| 6,387,069 | B1 * | 5/2002 | Utterberg ...................... 604/4.01 |
| 7,131,956 | B1 | 11/2006 | Pirazzoli et al. |
| 8,114,276 | B2 | 2/2012 | Childers |
| 2001/0048892 | A1 | 12/2001 | Bainbridge et al. |
| 2003/0152482 | A1 | 8/2003 | O'Mahony et al. |
| 2003/0163077 | A1 * | 8/2003 | Kim et al. .................... 604/5.01 |
| 2004/0149656 | A1 * | 8/2004 | Rovatti ................. A61M 1/168 210/636 |
| 2004/0243050 | A1 | 12/2004 | Treu et al. |
| 2005/0131332 | A1 * | 6/2005 | Kelly et al. .................. 604/4.01 |
| 2005/0230314 | A1 * | 10/2005 | Kim et al. ..................... 210/646 |
| 2006/0254982 | A1 * | 11/2006 | Kopperschmidt ............ 210/646 |
| 2008/0262405 | A1 * | 10/2008 | Ogihara et al. ............. 604/6.15 |
| 2009/0088675 | A1 * | 4/2009 | Kelly et al. .................. 604/4.01 |
| 2009/0101576 | A1 * | 4/2009 | Rohde et al. ................. 210/646 |
| 2009/0114593 | A1 | 5/2009 | Fischer |
| 2010/0042036 | A1 * | 2/2010 | Masaoka et al. .............. 604/6.1 |
| 2010/0078385 | A1 | 4/2010 | Kawarabata et al. |
| 2010/0130905 | A1 | 5/2010 | Nürnberger et al. |
| 2010/0234787 | A1 | 9/2010 | Masaoka |
| 2011/0132838 | A1 * | 6/2011 | Curtis et al. .................. 210/637 |
| 2011/0160637 | A1 | 6/2011 | Beiriger |
| 2011/0237997 | A1 * | 9/2011 | Beden et al. ................ 604/6.09 |
| 2012/0130299 | A1 * | 5/2012 | Knott et al. ................. 604/6.15 |
| 2012/0265117 | A1 | 10/2012 | Fava et al. |
| 2012/0271274 | A1 * | 10/2012 | Reiter et al. ................... 604/500 |
| 2013/0087210 | A1 * | 4/2013 | Brandl et al. ...................... 137/2 |

FOREIGN PATENT DOCUMENTS

| | | |
|---|---|---|
| DE | 100 11 208 C1 | 9/2001 |
| DE | 94 22 431 UI | 4/2002 |
| DE | 694 28 220 T2 | 6/2002 |
| DE | 196 55 224 B4 | 11/2006 |
| DE | 10 2006 022 1 | 11/2007 |
| DE | 10 2007 024 463 A1 | 11/2008 |
| DE | 196 55 230 B4 | 4/2009 |
| EP | 0 560 368 A2 | 9/1993 |
| EP | 0 829 265 A1 | 3/1998 |
| EP | 0 834 329 A1 | 4/1998 |
| EP | 1 110 566 A2 | 6/2001 |
| EP | 1 327 457 B1 | 7/2003 |
| EP | 1 457 218 A1 | 9/2004 |
| EP | 1 480 713 B1 | 12/2004 |
| EP | 1 892 000 A1 | 2/2008 |
| EP | 2 133 107 A1 | 12/2009 |
| EP | 2 218 470 A1 | 8/2010 |
| EP | 2 529 771 A2 | 12/2012 |
| JP | 2003 180823 A | 7/2003 |
| JP | 2005 218709 A | 8/2005 |
| WO | WO 92/02264 A1 | 2/1992 |
| WO | WO 96/40320 A1 | 12/1996 |
| WO | WO 01/08723 A1 | 2/2001 |
| WO | WO 03/082144 A2 | 10/2003 |
| WO | WO 2008/125893 A1 | 10/2008 |
| WO | WO 2011/081740 A1 | 7/2011 |

OTHER PUBLICATIONS

"Fresenius Medical Care North America Initiates Voluntary Recall of CombiSet True Flow Series™ Hemodialysis Blood Tubing Set with Priming Set and Transducer Protectors for use with the Blood vol. Monitor", Fresenius Medical Care, p. 1 (2011).

W. H. Horl et al.: "Replacement of Renal Function by Dialysis", 5th Edition, Drukker, Parsons and Maher, pp. 360, 363, 390-391 (2004).

* cited by examiner

METHOD FOR PRE-FILLING A HEMODIALYSIS APPARATUS

CROSS REFERENCE TO PRIOR APPLICATIONS

Priority is claimed to European Patent Application No. 12167382.6, filed May 9, 2012. The entire disclosure of said application is incorporated by reference herein.

FIELD

The present invention relates to a method for pre-filling a hemodialysis apparatus.

BACKGROUND

A hemodialysis apparatus comprises a dialysate side and a blood side. The dialysate side includes a dialysate source supplying the dialysate, either in the form of dialysate water mixed with additives by the hemodialysis apparatus or in the form of a dialysis supply. The dialysate chamber of a dialyzer with a membrane and a dialysate pump pumping the dialysate from the dialysate source to the dialysate chamber are further included on the dialysate side. Finally, a waste pump is provided on the dialysate side between the dialysate chamber and a waste tank or a waste discharge. The blood side includes the blood chamber of the dialyzer as well as a venous line and an arterial line which are connected to a respective one of the two ends of the dialyzer blood chamber.

A pre-filling liquid source is further provided which supplies the pre-filling liquid for pre-filling the venous and arterial lines. The pre-filling liquid source can be formed by the dialysate source, but may basically also be a separate pre-filling liquid source, for example, a bag containing a saline solution.

Prior to applying the venous and arterial lines or the respective cannulas to a patient, the two blood-side lines are pre-filled with pre-filling liquid, as is described, for example, in DE 196 55 224 B4. The introduction of the pre-filling liquid can be supported by a pump, for example, by the dialysate pump, which generally is configured as a displacement pump in the form of a peristaltic hose pump. There is therefore an inherent risk that, during the pre-filling, the fluid pressure in the venous and/or the arterial line increases to an extent, for example, because of a kinked line, that unallowable overpressures occur or the relevant line can be damaged and thereby become leaky. If the leak initially goes unnoticed, the effort in preparing the dialysis can increase substantially.

SUMMARY

An aspect of the present invention is to provide an improved method for pre-filling a hemodialysis apparatus.

In an embodiment, the present invention provides a method for pre-filling a hemodialysis apparatus which includes providing a hemodialysis apparatus comprising a pre-filling liquid source configured to supply a pre-filling liquid, a dialyzer, a dialysate side, a blood side. The dialysate side comprises a dialysate chamber of the dialyzer, a dialysate pump configured to pump the pre-filling liquid to the dialysate chamber, and a waste pump configured to pump the pre-filling liquid away from the dialysate chamber. The dialysate chamber comprises a dialyzer membrane. The blood side comprises an arterial line, a blood pump, a blood chamber of the dialyzer, and a venous line. A pressure sensor is arranged on the dialysate side or on the blood side. The arterial line and the venous line are pre-filled with the pre-filling liquid from the pre-filling liquid source by operating the dialysate pump. A blood-side fluid pressure is continuously determined via the pressure sensor during the pre-filling. The pre-filling is stopped when the blood-side fluid pressure determined by the pressure sensor exceeds or falls below a defined limit pressure.

BRIEF DESCRIPTION OF THE DRAWINGS

The present invention is described in greater detail below on the basis of embodiments and of the drawings in which.

DETAILED DESCRIPTION

Figure 1:
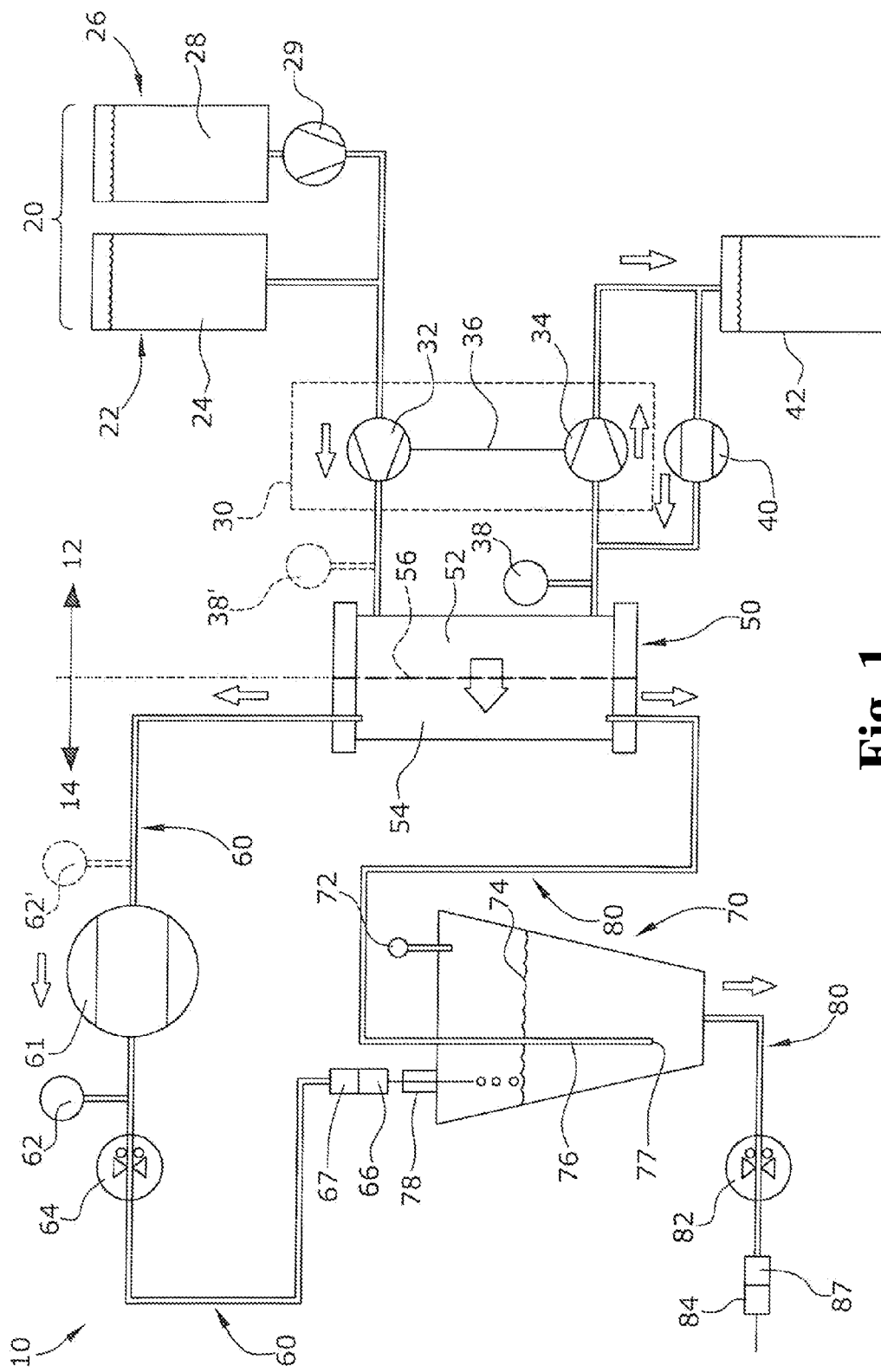
FIG. 1 shows a schematic illustration of a hemodialysis apparatus to illustrate a method for pre-filling the hemodialysis apparatus during the pre-filling of the arterial and the blood-side lines with pre-filling liquid.

On the dialysate side and/or on the blood side, at least one pressure sensor is provided. The pressure sensor can, for example, be provided on the blood side at a position along the arterial line and/or the venous line as an arterial or venous pressure sensor that detects the fluid pressure in the arterial or the venous line. During the pre-filling of the arterial and the venous line with pre-filling liquid from the pre-filling liquid source, the fluid pressure is continuously checked by, for example, the arterial or venous pressure sensor, the pre-filling being stopped as soon and as long as the blood-side fluid pressure measured by the relevant pressure sensor falls below or exceeds a defined limit pressure. The level of the defined limit pressure is chosen such that the risk of damage to the blood-side lines can be excluded as long as the blood-side fluid pressure does not fall below or exceed a defined limit pressure.

The risk of an excessive blood-side fluid pressure may result, for example, from the fact that the blood-side lines, which generally are of a flexible nature, are kinked so that the flow resistance increases at the relevant kink or the line is blocked completely at the kink. During pre-filling, this can be detected by a quasi-continuous monitoring, for example, of the blood-side fluid pressure in the arterial and/or venous line. Depending on the fluidic position of the relevant pressure sensor with respect to a pump, the fluid pressure detected by the pressure sensor increases or decreases in the case of an increased flow resistance in the blood-side lines. When the fluid pressure falls below or exceeds the limit pressure, pre-filling is stopped, on the one hand, and on the other hand, a corresponding alarm signal can be emitted.

In an embodiment of the present invention, the pre-filling liquid source can, for example, be formed by a dialysate source and, during pre-filling, the dialysate pump pumps the pre-filling liquid through the dialyzer membrane into the blood chamber and from there into the arterial and the venous line. The pre-filling liquid is thus not introduced from a separate pre-filling liquid tank directly into the blood-side lines, but is introduced indirectly, via the dialyzer, from the dialysate chamber into the blood chamber from where the pre-filling liquid flows into the two blood-side lines. This procedure offers the advantage that a separate pre-filling liquid tank can be omitted.

The pumps on the dialysate side, i.e., the dialysate pump and the waste pump, are designed as displacement pumps operating in a very precise and error-free manner, for example, as membrane pumps, piston pumps or balance chamber pumps. As a result of this fact, an increased flow resistance in one of the blood-side lines can lead to a dramatic increase in the fluid pressure in the relevant blood-side line. By monitoring the fluid pressure in the blood-side lines in a continuous and close manner with respect to time, such a dramatic pressure rise can immediately be detected, and the pump responsible for the filling fluid flow through the dialyzer membrane can be deactivated. The risk of an unnoticed damage and of air entrapments in or at the blood-side lines can thus be substantially reduced.

In a embodiment of the present invention, the dialysate pump can, for example, be coupled permanently, for example, by a forced coupling, with the waste pump to form a balancing pump. It is thereby mechanically provided that the dialysate pump always pumps exactly the same amount of liquid towards the dialyzer as the waste pump draws from the dialyzer. A separate ultra-filtration pump is further provided which is arranged fluidically in parallel with the waste pump. When the blood-side lines are pre-filled with pre-filling liquid, the ultra-filtration pump is operated in reverse flow, i.e., it pumps a part of the liquid pumped downstream by the waste pump back to the inlet side of the waste pump via a bypass. The pump rate of the ultra-filtration pump is here always below the pump rate of the waste pump, so that dialysate already used is not pumped backward into the dialyzer or into the blood-side lines.

In an embodiment of the present invention, the blood pump can, for example, be arranged in the arterial line or the venous line pumps towards a free line end at a pump rate lower than the pre-filling pump rate at which the pre-filling liquid passes through the dialyzer membrane from the dialysate chamber to the blood chamber. The pump rate of the blood pump may be chosen and set, for example, so that the arterial and venous lines fill evenly with pre-filling liquid or are filled completely with pre-filling liquid at about the same time.

In an embodiment of the present invention, prior to the beginning of the pre-filling, the venous line end can, for example, be connected directly with the arterial line or the arterial line can, for example, be connected directly with the venous line. In an embodiment of the present invention, an air trap can, for example, be arranged at a position along the venous line, the air trap comprising a pre-filling coupling for coupling the arterial line end during pre-filling. It may thus be provided that both blood-side lines are connected to the air trap during pre-filling so that air is removed from both lines in the air trap.

In an embodiment of the present invention, an actuable venous line clip can, for example, be provided at a position along the venous line between the air trap and the venous cannula. Between the venous line clip and the air trap, the line end of the arterial line is connected to the venous line or it is connected directly to the air trap. During pre-filling, a venting phase is provided which comprises the following method steps:
  stopping the pre-filling,
  closing the venous line clip, and
  operating the blood pump to pump the pre-filling liquid from the air trap through the venous line to the dialyzer blood chamber.

Firstly, pre-filling the blood side with pre-filling liquid is stopped, for example, by deactivating the ultra-filtration pump. No more pre-filling liquid passes from the dialysate side to the blood side. Due to the venous line clip thereafter being closed, the blood pump merely pumps or conveys the pre-filling liquid in the blood-side lines in a loop. In this manner, the entire volume of pre-filling liquid is pumped in a loop as often as desired in the blood-side line circuit so that the entire volume of pre-filling liquid passes the air trap a corresponding number of times so that all air can be removed from the blood-side lines in the air trap.

In an embodiment of the present invention, an arterial line clip can, for example, be provided between the dialyzer blood chamber and the arterial cannula. During the venting phase, the arterial line clip is closed and opened between the closing and the opening of the venous line clip. While the blood pump conveys the pre-filling liquid in the blood-side lines in a loop, the venous line clip is closed and the opened again. A pressure pulse is thereby induced into the pre-filling liquid column in the blood-side lines by which air bubbles trapped can be torn off and loosened and be entrained by the pre-filling liquid, the bubbles thus eventually being pumped into the air trap. Closing and opening the arterial line clip can be performed several times and at frequent short intervals so that a plurality of corresponding pressure pulses can be induced in a short time.

As an alternative or in addition thereto, the pump rate of the blood pump can be varied during the venting phase, for example, increased to twice the rate at a certain interval.

In an embodiment of the present invention, the dialyzer blood chamber or the dialyzer remains can, for example, be arranged or oriented vertically, without change, during the entire pre-filling process, and in particular during the venting phase, so that the vertical line is connected at the bottom of the blood chamber, while the arterial line is connected at the top of the blood chamber. Turning the dialyzer upside down, for example, for venting purposes, is no longer required. The handling during the pre-filling of the blood-side lines is thereby substantially facilitated and one source of errors is completely eliminated.

In an embodiment of the present invention, the venous pressure sensor can, for example, be arranged at the air trap. The venous pressure sensor may, for example, be configured as a pressure transducer that determines the pressure in the air volume within the closed air trap.

In an embodiment of the present invention, the air trap can, for example, comprise an immersion tube with a tube opening located below the liquid level, wherein the immersion tube is directly connected with the blood chamber of the dialyzer via a section of the venous line. Due to the tube opening being situated below the liquid level in the air trap, the air trap can be operated in both flow directions, i.e., also in reverse flow, without thereby allowing air to get into the blood-side lines from the air volume above the liquid level. The air trap is operated in reverse flow, in particular during the venting phase.

The following is a detailed description of an embodiment of the method of the present invention with reference to the drawings.

Figure 2:
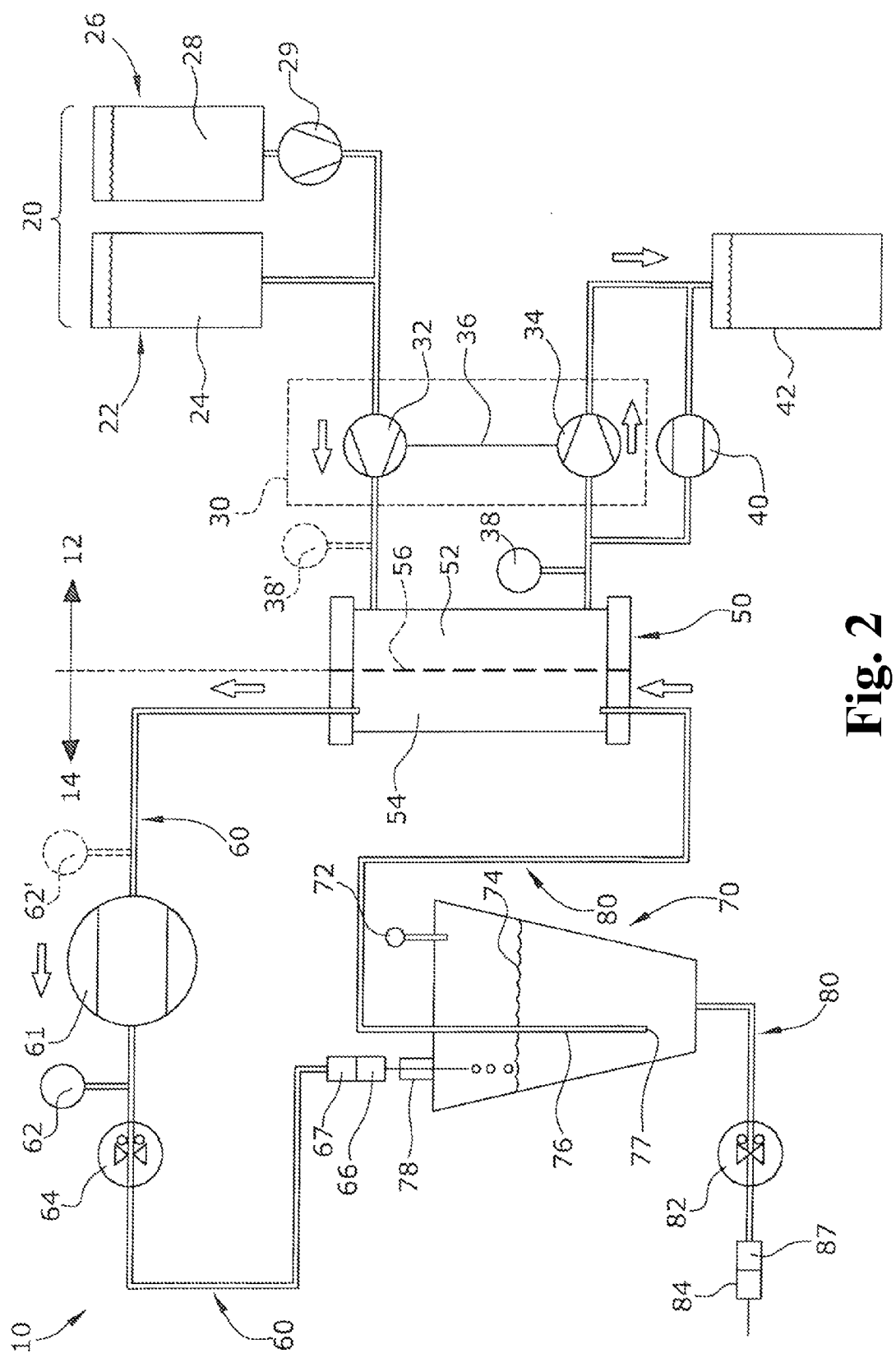
FIG. 2 shows a schematic illustration of the hemodialysis apparatus of FIG. 1 during a venting phase.

FIGS. 1 and 2 schematically illustrate a hemodialysis apparatus 10 which, with respect to its function, can be divided into a dialysate side 12 and a blood side 14. The border between the dialysate side 12 and the blood side 14 is formed by a dialysis membrane 56 in a dialyzer 50. In the dialyzer 50, the dialysis membrane 56 separates a dialysate chamber 52 from a blood chamber 54.

The dialysate side 12 comprises a pre-filling liquid source 20 supplying a pre-filling liquid. In the present case, the pre-filling liquid source 20 is also a dialysate source supplying dialysate for dialysis. The pre-filling liquid source 20 is formed by a dialysis water tank 22 containing dialysis water 24 and an additive tank 26 containing a dialysate additive 28. An additive pump 29 is arranged downstream of the additive tank 26, which pump, when needed, supplies the dialysate additive 28 to the dialysis water flow in a well dosed manner. It is also possible to provide a plurality of additive tanks, with the additives, in particular, being electrolytes and buffer substances. As an alternative to the dialysis water tank 22, the dialysis water can also be supplied from a water treatment device (not illustrated) in which the dialysis water is prepared from tap water from the public supply network.

The dialysate or the identical pre-filling liquid from the pre-filling liquid source 20 is pumped into the dialysate chamber 52 of the dialyzer 50 by a dialysate pump 32. From the dialysate chamber 52, a line extends to a waste pump 34 pumping the dialysate or the pre-filling liquid from the dialysate chamber 52 into a waste tank 42, where the used dialysate or the excess pre-filling liquid is stored. An ultra-filtration pump 40 is arranged fluidically parallel to the waste pump 34, which ultra-filtration pump 40 can be operated in both directions, i.e., in reverse flow and in parallel flow with respect to the waste pump 34.

The dialysate pump 32 and the waste pump 34 are mechanically connected via a mechanical connection 36 so that the pump rates of the dialysate pump 32 and the waste pump 34 are always absolutely identical. In this manner, the dialysate pump 32 and the waste pump 34 form a so-called balancing pump 30. The mechanical connection 36 may be realized, for example, by designing the balancing pump 30 as a membrane pump, wherein the one side of the pump membrane forms the pump chamber of the dialysate pump 32 and the other side of the pump membrane forms the pump chamber of the waste pump 34. When the ultra-filtration pump 40 is operated in reverse flow, pre-filling liquid is pumped at exactly the pump rate of the ultra-filtration pump 40 from the blood side 12 through the dialyzer membrane 56 to the dialysate side 14. A pressure sensor 38 is arranged between the dialysate chamber 52 and the waste pump 34.

On the blood-side 14 of the dialyzer membrane 56, the blood chamber 54 of the dialyzer 50 is situated into which an arterial line 60 and a venous line 80 open. The dialyzer 50 is fixed vertically on the hemodialysis apparatus 10 so that the flow direction is oriented vertically both in the blood chamber 54 and in the dialysate chamber 52 and, during hemodialysis, is the reverse flow.

Arranged at a position along the arterial line 60 is a blood pump 61 designed as a peristaltic hose pump and adapted to be operated in both pumping directions. The pumping direction and the pump rate of the blood pump 61 are controlled by an apparatus control unit which is not illustrated herein. Further along the arterial line 60, an arterial pressure sensor 62 is provided which detects the static fluid pressure in the arterial line downstream of the blood pump 61. The arterial pressure sensor 62' may also be arranged between the blood pump 61 and the dialyzer 50. The arterial pressure sensor 62 is also connected with the apparatus control unit. Downstream of the arterial pressure sensor 62, an arterial hose clip 64 is arranged which is adapted to close and open the arterial line 60 which is designed as a flexible hose. An arterial cannula 66 is applied at an appropriate time at the line end 67 of the arterial line 60, the arterial cannula 66 comprising a needle with which the arterial line 60 can be set to a blood vessel of a patient from whom the blood pump 61 draws patient blood into the arterial line 60 for the actual hemopurification.

A conical air trap 70 is arranged at a position along the venous line 80, comprising a central and rigid immersion tube 76 with a tube opening 77 which opens downward. The tube opening 77 is situated far below a liquid level 74 whose height is controlled to a nominal level via a separate upper gas connector (not illustrated) and a level regulating pump (not illustrated) connected thereto. It is thereby provided that the tube opening 77 is always situated below the liquid level 74. It is provided that the air trap 70 can generally be operated in both directions.

A venous pressure sensor 72 is further arranged at the air trap 70, which pressure sensor detects the fluid pressure in the venous line 80. The air trap 70 finally also comprises a pre-filling coupling 78 to which the arterial line end 67 or, as the case may be, the arterial cannula 66 can be connected. During the entire pre-filling of the hemodialysis apparatus 10, the arterial line end 67 or the arterial cannula 66 remains connected to the pre-filling coupling 78. Only for the actual hemopurification is the arterial line end 67 or the arterial cannula 66 removed from the pre-filling coupling 78 and is connected to an arterial blood vessel of the patient via the arterial cannula 66.

Further along the venous line 80, which is designed as a flexible hose, a venous line clip 82 is provided which is connected with the apparatus control unit and represents a switchable valve that closes or opens the venous line 80. At the free line end 87 of the venous line 80, a venous cannula 84 is provided which comprises a needle so that the cannula can be connected with a corresponding venous blood vessel of the patient at the beginning of the actual hemodialysis.

At start-up of the hemodialysis apparatus, the blood-side lines 60, 80 which are designed as disposable articles, are first applied to the hemodialysis apparatus 10. Thereafter, the arterial line end 67 or the arterial cannula 66 is coupled to the pre-filling coupling 78 of the air trap 70. The pre-filling of the hemodialysis apparatus 10 can now be started by activating the balancing pump 30. The pre-filling liquid composed of the dialysis water 24 and the dialysate additive 28 is thereby pumped into the dialysate chamber 52 of the dialyzer 50 by the dialysate pump 32, and is pumped from there into the waste tank 42 by the waste pump 34. The pump rate of the balancing pump 30 is, for example, 500 ml/min. As soon as the pre-filling liquid reaches the waste tank 42, the ultra-filtration pump 40 is activated in reverse flow with a pump rate below the pump rate of the balancing pump, for example, with 400 ml/min.

The pre-filling liquid thereby passes from the dialysate chamber 52 through the dialyzer membrane 56 into the blood chamber 54 at a pre-filling pump rate corresponding to the pump rate of the ultra-filtration pump. The blood pump 61 is driven at a pump rate no higher than the pre-filling pump rate, for example, at 200 ml/min, so that half of the pre-filling liquid flow flows from the blood chamber 54 into the arterial line 60 and into the venous line 80, respectively. The two line clips 64, 82 are open at that time. This state is called pre-filling and is illustrated in FIG. 1.

During pre-filling, the apparatus control unit continuously determines and controls the fluid pressure in the arterial line 60 and in the venous line 80 via the pressure sensors 62, 72. As soon as the measured fluid pressure exceeds a defined limit pressure, pre-filling is stopped in order to prevent damage to the arterial line 60 and/or the venous line 80 or a bursting thereof. The defined limit pressure can be exceeded, in particular, when one of the blood-side lines 60, 80 is kinked. In addition or as an alternative thereto, the fluid pressure can also be detected by means of one or a plurality of dialysate-side pressure transducers 38; 38'.

A venting phase, illustrated in FIG. 2, is provided at the end of the pre-filling or as an interruption of the pre-filling. The ultra-filtration pump 40 is here stopped so that no pre-filling liquid passes through the dialyzer membrane 56. The pump rate of the balancing pump 30 can be reduced, for example, to 100 ml/min in the venting phase. Simultaneous to the stopping of the ultra-filtration pump 40, the venous line clip 82 is closed, so that the pre-filling liquid can no longer flow from the air trap 70 to the venous line end 87 or a discharge bag or discharge port connected thereto. The blood pump 61 is still operated in the same direction as during pre-filling, so that the pre-filling liquid is pumped in a loop, with the pre-filling liquid entering the dialyzer blood chamber 54 at the lower end of the dialyzer blood chamber 54 through the venous line 80 and leaving the blood chamber 54 at the vertical top end to enter the arterial line 60. In the blood chamber 54, a pre-filling liquid flow is created running vertically upward from below, the flow entraining air bubbles in their direction of buoyancy.

In this manner, air bubbles are removed from the blood chamber 54, which are eventually removed for good from the pre-filling liquid flow in the air trap 70. In the venting phase, the arterial line clip 64 is closed and opened periodically so as to thereby induce pressure pulses into the closed pre-filling liquid circuit. As an alternative or in addition thereto, it is also possible to rhythmically vary the pump rate of the blood pump 61, for example, 200 ml/s and 400 ml/s, whereby pressure pulses are induced into the lines. The pressure pulses induced improve the detaching of the air bubbles in the entire circuit and in particular in the blood chamber 54. During the entire pre-filling process, including the venting phase(s), the dialyzer 50 remains unchanged in a vertical orientation and does not have to be rotated by 180° to be vented. The venous line 80 thus always remains connected with the blood chamber 54 at the bottom, relative to the vertical orientation, and the arterial line 60 always remains connected with the blood chamber 54 at the top.

After the venting phase, the pre-filling of the hemodialysis apparatus can be ended or the pre-filling can be continued. When the pre-filling is ended, the arterial cannula 66 is uncoupled from the coupling 78 and applied to the relevant blood vessel of the patient. The applied venous cannula 84 can also be plied to the relevant blood vessel of the patient so that the hemopurification of the patient can be started.

The present invention is not limited to embodiments described herein; reference should be had to the appended claims.

What is claimed is:

1. A method for pre-filling a hemodialysis apparatus, the method comprising:
    providing a hemodialysis apparatus comprising:
        a pre-filling liquid source configured to supply a pre-filling liquid,
        a dialyzer,
        a dialysate side comprising:
            a dialysate chamber of the dialyzer, the dialysate chamber comprising a dialyzer membrane,
            a dialysate pump configured to pump the pre-filling liquid to the dialysate chamber, and
            a waste pump configured to pump the pre-filling liquid away from the dialysate chamber,
        a blood side comprising:
            an arterial line comprising an arterial line end,
            a blood pump,
            a blood chamber of the dialyzer, and
            a venous line comprising a venous line end, and
        a pressure sensor arranged on the dialysate side or on the blood side;
    connecting the venous line end directly to the arterial line or connecting the arterial line end directly to the venous line;
    pre-filling the arterial line and the venous line with the pre-filling liquid from the pre-filling liquid source by operating the dialysate pump; and
    continuously determining a blood-side fluid pressure via the pressure sensor during the pre-filling,
wherein,
    the pre-filling is stopped when the blood-side fluid pressure determined by the pressure sensor exceeds or falls below a defined limit pressure, and
    the venous line end is not directly connected to the arterial line end.

2. The method as recited in claim 1, wherein the pressure sensor is at least one of an arterial pressure sensor arranged along the arterial line and a venous pressure sensor arranged along the venous line.

3. The method as recited in claim 1, wherein the pre-filling liquid source is a dialysate source, and the method further comprises pumping the pre-filling liquid with the dialysate pump through the dialyzer membrane into the arterial line and into the venous line during the pre-filling.

4. The method as recited in claim 1, wherein the dialysate pump is coupled to the waste pump so as to form a balancing pump, the hemodialysis apparatus further comprises a separate ultra-filtration pump which is configured to be fluidically parallel to the waste pump, and wherein, during the pre-filling, the ultra-filtration pump is configured to operate in a reverse flow relative to the waste pump.

5. The method as recited in claim 1, wherein the arterial line comprises an arterial line end, and wherein, during the pre-filling, a pumping rate of the blood pump towards the arterial line end is no higher than a pre-filling pumping rate at which the pre-filling liquid flows through the dialyzer membrane.

6. The method as recited in claim 1, wherein the hemodialysis apparatus further comprises an air trap arranged along the venous line, the air trap comprising a pre-filling coupling which is configured to connect to the arterial line end during the pre-filling.

7. The method as recited in claim 6, wherein the hemodialysis apparatus further comprises a venous line clip configured to be actuatable and which is arranged in the venous line between the air trap and the venous line end, and wherein the method further comprises a venting phase comprising:
    stopping the pre-filling;
    closing the venous line clip; and
    operating the blood pump so as to pump the pre-filling liquid from the air trap through the venous line to the blood chamber.

8. The method as recited in claim 7, wherein, during the venting phase, a pumping rate of the blood pump is varied at least once by at least 30%.

9. The method as recited in claim 7, wherein the hemodialysis apparatus further comprises an arterial cannula arranged on the arterial line at the arterial line end and an arterial line clip arranged between the blood chamber and the arterial cannula, and wherein, during the venting phase between the closing of the venous line clip and the opening of the venous line clip, the method further comprises closing and opening the arterial line clip.

10. The method as recited in claim 9, wherein the blood chamber remains in a vertical orientation during the pre-filling so that the venous line is connected at a bottom of the blood chamber, and the arterial line is connected at a top of the blood chamber.

11. The method as recited in claim 6, wherein the pressure sensor is a venous pressure sensor which is arranged at the air trap.

12. The method as recited in claim 11, wherein the air trap comprises an immersed tube with a tube opening arranged below a liquid level, the immersed tube being connected directly with the blood chamber of the dialyzer via a section of the venous line.

* * * * *